United States Patent [19]
Gerber et al.

[11] Patent Number: 6,055,871
[45] Date of Patent: May 2, 2000

[54] MACHINE FOR CUTTING A CYLINDRICAL SPECIMEN OF ROCKET PROPELLANT

[75] Inventors: Robert L. Gerber; Norman G. Zweirzchowski, both of Ridgecrest; Herbert P. Richter, Oceanside; Larry R. Boyer, Inyokern, all of Calif.

[73] Assignee: The United States of America as represented by the Secretary of the Navy, Washington, D.C.

[21] Appl. No.: 09/076,984

[22] Filed: May 13, 1998

[51] Int. Cl.[7] ........................................................ G01N 1/04
[52] U.S. Cl. ........................ 73/864.41; 83/200.1; 83/167; 83/919
[58] Field of Search ................................ 73/104, 864.41; 83/919, 651.1, 200.1, 167; 425/289; 30/115, 116

[56] References Cited

U.S. PATENT DOCUMENTS

| | | | |
|---|---|---|---|
| 4,160,314 | 7/1979 | Fridy | 83/651.1 X |
| 4,598,597 | 7/1986 | Widner et al. | 83/919 X |
| 5,103,684 | 4/1992 | Denton | 30/301 X |

*Primary Examiner*—Rinaldi I. Rada
*Assistant Examiner*—Ana Luna
*Attorney, Agent, or Firm*—Gregory M. Bokar; David S. Kalmbaugh; Anthony J. Serventi

[57] ABSTRACT

A machine provides in situ cutting of a specimen of elastomeric propellant from a rocket motor wherein an undetached plug is formed by an annular opening cut through the motor casing and into the propellant. The machine has a length of resilient wire secured at its ends to a rod for forming a loop mounted on the rod. The rod is inserted into the opening at one side of the plug with the loop around the plug. The rod is then rotated to wind the wire onto the rod so as to contract the loop and sever the plug. A tray is pivotally mounted on the rod between the rod and the plug with the wire passing through slots in the tray. The tray is inserted into the opening beside the specimen so as to prevent engagement of the rod with the specimen during cutting and to receive the detached specimen for removal from the motor. The rod and tray extend from an assembly having an air motor rotating the rod through reduction gearing and through an overrunning clutch which drives in the loop contracting direction. This assembly is mounted so that a load cell measures the torque being applied to sever the plug. When the specimen is severed, the air motor is reversed allowing the resilient energy stored in the wire to dissipate as the wire unwinds. When the wire is fully unwound, the overrunning clutch prevents winding the wire in the reverse direction.

3 Claims, 3 Drawing Sheets

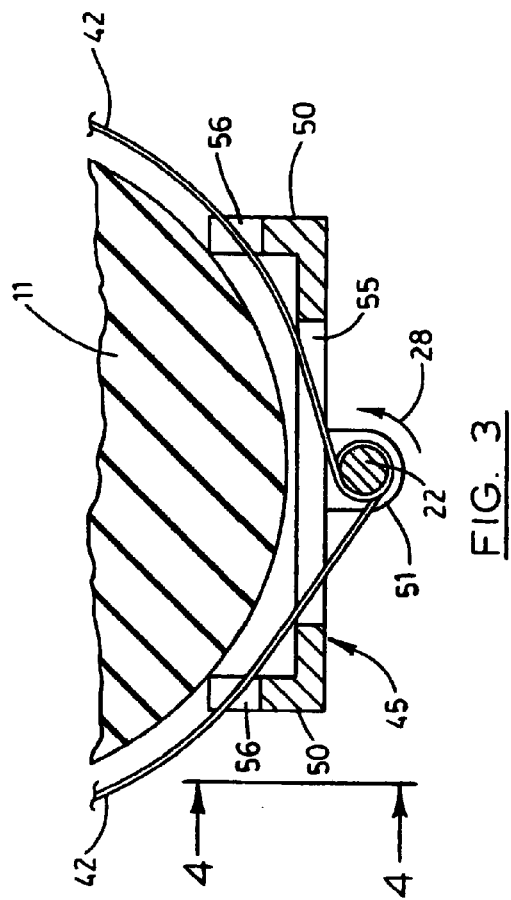
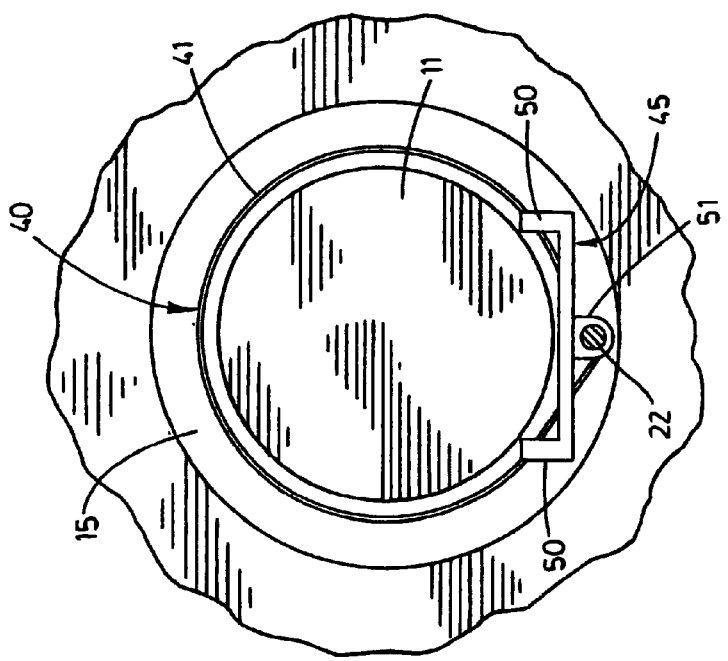

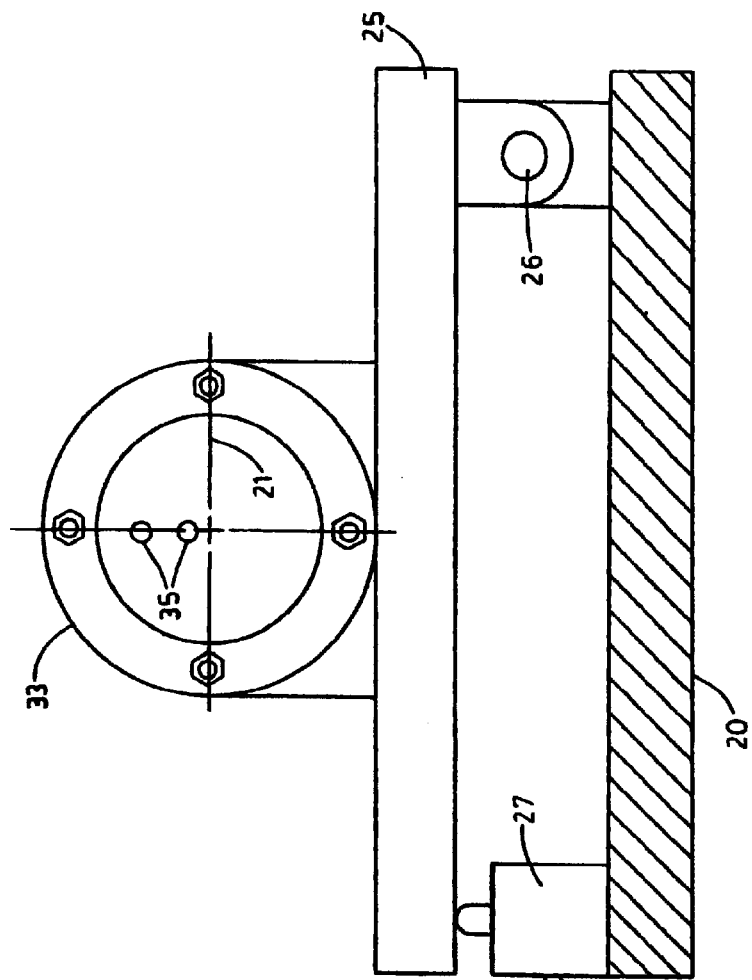
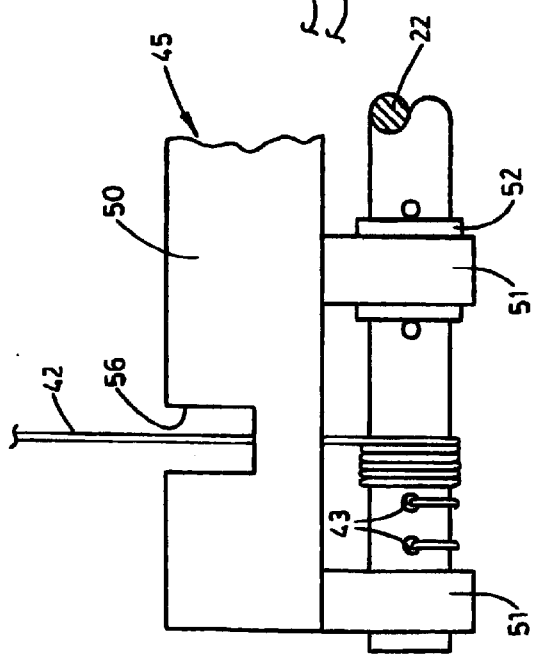
FIG. 5
FIG. 4

MACHINE FOR CUTTING A CYLINDRICAL SPECIMEN OF ROCKET PROPELLANT

BACKGROUND OF THE INVENTION

1. Field of the Invention

The present invention pertains to devices for cutting elastomeric materials; and, more particularly, pertains to such devices for in situ sampling of specimens of solid propellant in a rocket motor.

2. Description of the Prior Art

Large, military, solid propellant, rocket motors must be stored for decades and yet function with full effectiveness. To ensure this effectiveness, samples of the propellant are taken regularly from substantially complete serviceable or specimen motors for testing to determine if the propellant has remained stable. The propellants of interest are elastomers which are very tough and elastic so as to retain their shape and function despite shocks in transportation and the intense vibrations and thermal stresses that occur following ignition. The propellant is, typically, a single large "grain" cast within a generally cylindrical casing.

Because of the mechanical properties of these elastomeric propellants, the large size of the motors and samples, the inaccessibility of the propellant within the casing, and the dangers of ignition or detonation involved in cutting energetic materials, the prior art has no completely satisfactory method or device for obtaining the necessary samples.

It is known to obtain a cylindrical specimen of such propellant adjacent to the casing by, initially, cutting an annular opening through the casing and into the propellant to form a plug or core of the propellant; and then detaching the specimen. One method of detaching the specimen is by successive cuts with a wire mounted on two hydraulically powered arms, a method ineffective with highly elastic propellant which deforms without being severed. A second method effective with highly elastic propellants uses a wire loop which is inserted into the opening about the plug and which is contracted to cut off the plug, the loop being connected at one point to a rod which is rotated to wind the wire onto the rod and thus contract the loop. However, this second method damages the specimen by embedding the rod therein and is dangerous due to subsequent uncontrolled release of resilient energy stored in the wire as it was wound onto the rod.

BRIEF SUMMARY OF THE INVENTION

Accordingly, an object of the present invention is to provide for the effective cutting of a cylindrical specimen of solid propellant, which is tough and highly elastic, from a grain of such propellant.

Another object is to provide such cutting without damage to the specimen.

An additional object is to provide for the convenient removal of the specimen after such cutting.

Still another object is to provide such cutting where the force and rate of cutting are controllable.

Yet another object is to provide such cutting by the contraction of a wire loop without subsequent uncontrolled release of resilient energy stored in the wire.

Further objects are to provide improved elements and arrangements thereof in a machine which is fully effective for cutting off a cylindrical specimen of rocket propellant.

These and other objects and advantages are provided by a machine for cutting a cylindrical specimen of propellant from a rocket motor in which an undetached plug has been formed by an annular opening cut through the motor casing and into the propellant. The machine has a length of resilient wire secured at its ends to a rod so as to form a loop mounted at one point on the rod so that the rod may be inserted into the annular opening beside the plug with the loop around the plug. The machine has a tray pivotally mounted on the rod between the rod and the plug with the wire passing through slots in the tray so that the tray may be inserted into the opening together with the rod.

The rod and tray extend from a driving assembly having a reversible air motor, high reduction gearing, and an overrunning clutch. The air motor drives the gearing which drives the overrunning clutch which rotates the rod in the loop contracting direction. The driving assembly is pivotally mounted adjacent to a load cell for measurement of the torque being applied to sever the plug.

In operation, the rod, tray, and loop are inserted into the annular opening in the rocket motor with the loop around the plug and the rod and tray at one side of the opening. The air motor is then energized in a forward direction so that the rod rotates to wind the wire thereon so as to contract the loop and sever the plug. As this takes place, the tray prevents engagement of the rod with the specimen so that the rod does not embed in the specimen or otherwise damage it. The forward rotation of the air motor is stopped when the plug is severed.

At this point, the resilient energy stored in the wire by being wound on the rod is restrained through the overrunning clutch by the high reduction gearing. The air motor is then reversed allowing this energy to dissipate as the wire unwinds. When the wire is fully unwound, the overrunning clutch prevents winding the wire on the rod in the reverse direction if the motor continues in this reverse direction before being deenergized.

When the wire is unwound, the specimen is removed from the annular opening.

BRIEF DESCRIPTION OF THE SEVERAL VIEWS OF THE DRAWING

FIG. 2 is a view on line 2—2 of FIG. 1 showing elements of the machine disposed in the annular opening.

FIG. 3 is a sectional view from the position of line 3—3 of FIG. 1 and at an enlarged scale showing portions of the machine elements and of a plug of rocket propellant.

FIG. 4 is a fragmentary view of the FIG. 3 machine element portions from the position of line 4—4 of FIG. 3.

FIG. 5 is a view of the machine along an axis thereof from the position of line 5—5 of FIG. 1.

DETAILED DESCRIPTION OF THE INVENTION

Figure 1:
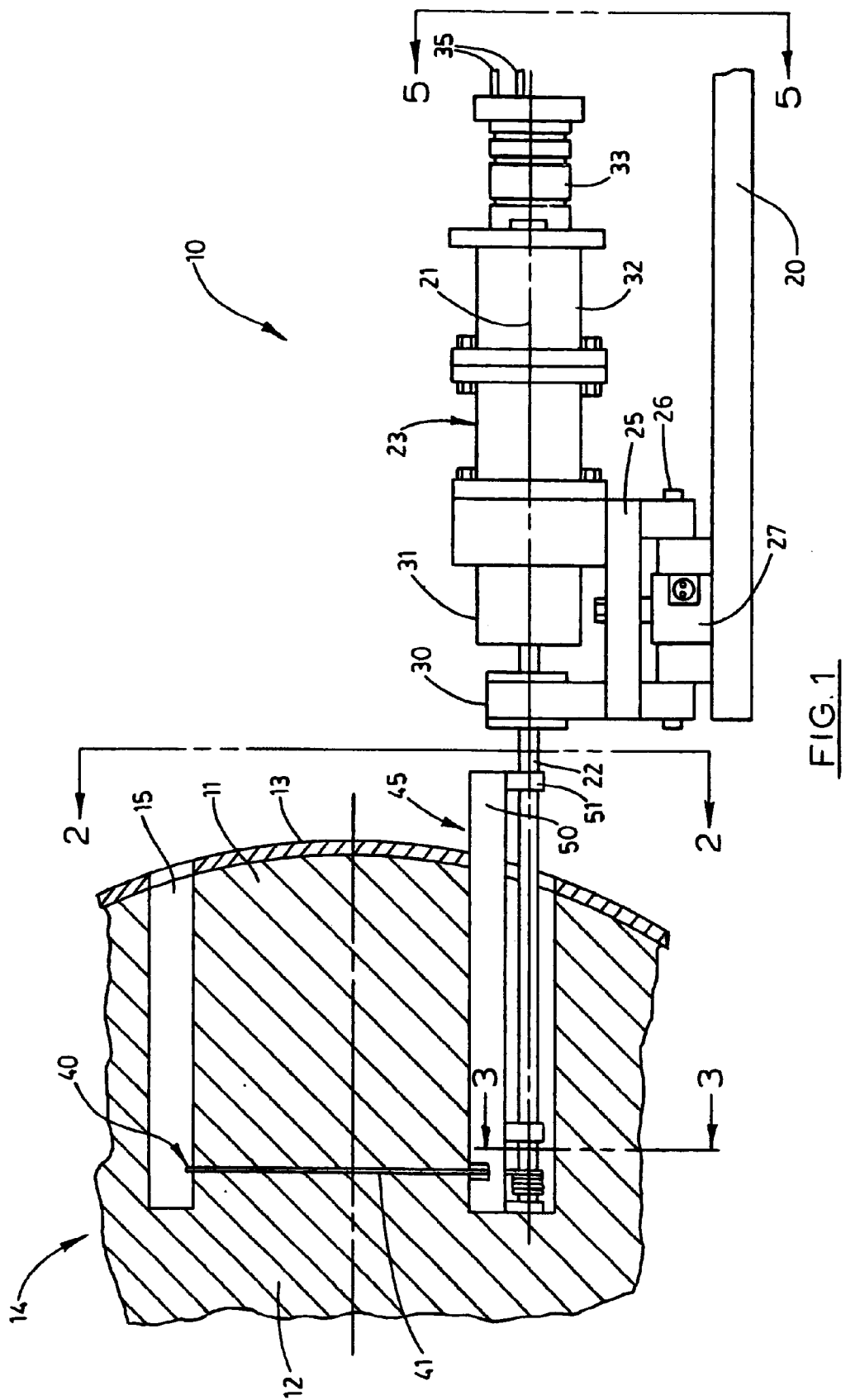
FIG. 1 is a somewhat schematic elevation of a machine embodying the principles of the present invention for cutting a cylindrical specimen of propellant from a rocket motor, the machine being shown in operating relation with a representative and fragmentarily represented rocket motor having an annular opening cut therein.

Referring more particularly to FIGS. 1 and 2, numeral 10 indicates a machine embodying the principles of the present invention for cutting a core or cylindrical plug 11 from a mass of elastomeric propellant 12 disposed in a casing 13 of a rocket motor indicated generally by the numeral 14. An annular opening 15 has been cut through the casing and into the propellant in so as to form the plug. The opening is thus in circumscribing relation to the plug which is of cylindrical shape and, at one axial end, is attached to the balance of the propellant as a projection therefrom.

Machine 10 has a base 20 shown in FIGS. 1 and 5 and supported in any suitable manner so that the machine is disposed for operation with an axis 21 of the machine directed into the opening 15 parallel to the axis of the undetached plug 11 at one side of the plug; typically the lower side. The machine has a torque rod 22 which extends from and is supported and powered by a rotational driving assembly 23. The rod and assembly extend along axis 21 with the rod extended into opening 15. The base provides, in any suitable manner, for translational movement of the rod and driving assembly along axis 21. The assembly is fixed to a plate 25 which is mounted on base 20 by a pivot 26 spaced transversely of axis 21 so that a load cell 27 disposed between the base and the plate is loaded when the rod is driven by the assembly in a forward or cutting direction indicated in FIG. 3 arrow 28.

Driving assembly 23 has a bearing 30, an overunning clutch 31, a high ratio reduction gear box 32, and an air motor 33 which are disposed in spaced and rotationally connected succession along axis 21 from rod 22. Only the exteriors of elements 30–33 are depicted since any one of various suitable constructions known in the art may be utilized.

Air motor 33, which is sometimes referred to in the claims as "a powered rotational driving device", is reversible, as by applying air pressure to a selected one of its two ports 35, and is thus energizable to rotationally drive rod 22 either in direction 28 or in the opposite or reverse direction. The rotational speed of the motor is selected by controlling the air pressure applied thereto; and the motor is, of course, deenergized when no air pressure is applied to either port.

Motor 33 rotationally drives clutch 31 through a high reduction ratio which is provided by gear box 32 and which frictionally prevents rotation of the motor in either direction by torque applied to rod 22 when the motor is not energized. A reduction ratio of 2000 to 1 has been found effective to so limit rotation of the unenergized motor.

Overrunning clutch 31 is constructed so as to transmit torque from motor 33 through gear box 32 to drive rod 22 in direction 28 and, as conventional with overrunning clutches, to transmit torque in the opposite direction from the rod to the gear box and motor. However, the clutch overruns so that the rod is not driven in this opposite direction by the motor.

Bearing 30 serves to support torque rod 22 together with other elements of machine 10 mounted on the rod and shown in FIGS. 1–4. These elements include a length 40 of wire depicted with its central portion disposed in a loop 41 positioned by the other elements of the machine in a plane generally normal to axis 21 and within opening 15 so as to circumscribe plug 11. The wire has opposite end portions 42 which, as best shown in FIGS. 3 and 4, extend through corresponding bores 43 disposed diametrically of rod 22. The wire is thus attached to the rod so that rotation thereof in direction 28 winds both of the wire end portions in the same direction onto the rod to contract the loop and cut the plug from the balance of the elastomeric propellant 12.

Length 40 is constructed of a flexible, tensionable, and resilient material such as steel music wire. Such wire having a diameter of 0.059 inch (1.5 mm.) has been found effective to sever a plug, such as plug 11, having a diameter of 8.7 inches (22 cm.) in about 30 minutes when the wire is wound about a torque rod corresponding to rod 22 and driven at about 4 minutes per revolution.

Machine 10 has a tray which is indicated generally by numeral 45 and which is mounted on rod 22 for movement therewith along axis 21 and for pivotal movement relative to the rod about axis 21. As shown in FIGS. 1 and 2 the tray is dimensioned and proportioned so as to be disposed in annular opening 15 between the rod and plug 11 when loop 41 is positioned in the above-described circumscribing relation for severing the plug.

Transversely, tray 45 has opposite sides 50 turned toward plug 11 so as to receive it when severed. As best shown in FIGS. 3 and 4, the tray extends along rod 22 at the region thereof which has the bores 43 and onto which the length 40 of wire is wound. The tray has a three lugs 51 extended oppositely of the loop and pivotally fitted to the rod, and the tray is positioned axially on the rod by any suitable arrangement 52, such as washers and cotter pins.

Tray 45 has a central slot 55 adjacent to rod 22 and has a pair of slots 56 individual to tray sides 50. Wire end portions 42 extend from the rod through the central slot and then individually through the side slots to loop 41.

OPERATION

The operation of the described embodiment of the subject invention is believed clearly apparent and is briefly summarized at this point. After the annular opening 15 is cut, machine 10 is positioned as depicted in FIGS. 1 and 2 and as previously described with rod 22, tray 45, and loop 41 inserted into the opening 15 with the loop around the plug and the rod and tray at one side of the opening. Air motor 33 is then energized to drive rod 22 in direction 28 through overrunning clutch 31 so as to contract the loop and sever the plug. As this takes place, tray 45 prevents engagement of the rod with the plug so that rod does not embed in the plug, and the torque being applied to sever the plug is measured by reaction of this torque against load cell 27 so that the force and rate of severing may be controlled by the air pressure applied to motor 33.

When plug 22 is severed, motor 33 is deenergized. At this point, the plug is received on the tray. However, at this point winding of the length 40 of wire onto rod 22 has stored in the wire resilient energy urging the rod to rotate oppositely of direction 28. With the air motor 33 unenergized, this resilient energy is restrained from unwinding the wire by the high reduction ratio of gear box 32 acting on the rod through the overrunning clutch 31.

To safely dissipate this stored resilient energy, air motor 33 is energized in the direction corresponding to the rotation of rod 22 in the direction opposite direction 28. This allows the wire to unwind by driving the rod in this opposite direction by torque transmitted through the overrunning clutch 31 to gear box 32 which limits the rotational speed of unwinding to that allowed by controlling the speed of the air motor in this opposite direction.

When the length 40 of wire is fully unwound and if air motor 33 were not immediately deenergized, continued rotation of rod 22 in the reverse or unwinding direction tends to rewind the wire in that direction. However, such rewinding is prevented by overrunning clutch 31 rotationally releasing the rod from the gear box 32 and motor when they continue in this reverse direction before the motor is deenergized.

When the wire is unwound, machine 10 is moved along axis 21 away from rocket motor 14 so that plug 11, which tray 45 has prevented from being damaged, is withdrawn on the tray from within opening 15. The plug is then conveniently accessible without any danger due to uncontrolled release of resilient energy stored as loop 40 is contracted.

Although machine 10 has been shown and described in what is conceived as the preferred embodiment, it is to be understood that the invention may be practiced within the scope of the following claims other than as specifically set forth herein.

What is claimed is:

1. A machine for cutting a cylindrical specimen of a propellant from a rocket motor wherein an undetached plug is formed by an annular opening cut through a casing of said rocket motor and into said propellant, said machine comprising:

a rod positioned on a machine axis which extends into said annular opening;

a resilient wire having first and second ends, the first and second ends of said resilient wire being secured to said rod to form a loop, said loop being disposed in a plane normal to said machine axis;

an air motor coupled to said rod;

said rod being inserted into said annular opening at one side of said undetached plug, said loop being positioned around said undetached plug;

said air motor rotating said rod in a first direction to wind said wire onto said rod which contracts said loop severing said cylindrical specimen from said propellant; and a tray pivotally mounted on said rod, said tray being adapted for movement with said rod along said machine axis;

said tray being inserted into said annular opening adjacent to said cylindrical specimen to receive said cylindrical specimen for movement away from said propellant when said cylindrical specimen is severed from said propellant.

2. The machine of claim 1 further comprising:

an overrunning clutch connected between said air motor and said rod, said overrunning clutch transmitting torque from said air motor to said rod when said air motor rotates said rod in said first direction and a reverse direction from said first direction; and said overrunning clutch preventing a reverse winding of said resilient wire on said rod when said air motor is operating in said reverse direction after said resilient wire is completely unwound from said rod and said air motor is de-energized.

3. The machine of claim 1 wherein said air motor comprises a reversible motor energized by pressurized fluid.

* * * * *